United States Patent
Barnes et al.

(10) Patent No.: US 8,029,570 B2
(45) Date of Patent: Oct. 4, 2011

(54) IMPLANTATION OF MAGNETS IN BONE TO REDUCE CONTACT PRESSURE

(75) Inventors: Darryl E. Barnes, Rochester, MN (US); David G. Lewallen, Rochester, MN (US); Kenton R. Kaufman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 146 days.

(21) Appl. No.: 10/254,232

(22) Filed: Sep. 25, 2002

(65) Prior Publication Data
US 2004/0059423 A1 Mar. 25, 2004

Related U.S. Application Data

(60) Provisional application No. 60/326,122, filed on Sep. 28, 2001.

(51) Int. Cl.
*A61F 2/30* (2006.01)
(52) U.S. Cl. .................................................. 623/18.12
(58) Field of Classification Search ................. 623/18.12
See application file for complete search history.

(56) References Cited

U.S. PATENT DOCUMENTS

| | | | |
|---|---|---|---|
| 4,024,588 A | 5/1977 | Janssen et al. | |
| 4,332,037 A | 6/1982 | Esformes et al. | |
| 4,479,271 A | 10/1984 | Bolesky et al. | |
| 4,644,942 A * | 2/1987 | Sump | 623/23.55 |
| 4,693,721 A * | 9/1987 | Ducheyne | 623/23.54 |
| 4,743,264 A | 5/1988 | Sherva-Parker | |
| 5,062,855 A | 11/1991 | Rincoe | |
| 5,092,320 A | 3/1992 | Maurer | |
| 5,507,835 A * | 4/1996 | Jore | 623/36 |
| 5,571,195 A | 11/1996 | Johnson | |
| 5,595,563 A | 1/1997 | Moisdon | |
| 5,879,386 A | 3/1999 | Jore | |
| 6,013,071 A | 1/2000 | Moisdon | |
| 6,032,677 A * | 3/2000 | Blechman et al. | 128/899 |
| 6,387,096 B1 | 5/2002 | Hyde, Jr. | |

* cited by examiner

*Primary Examiner* — Thomas J Sweet
*Assistant Examiner* — Christopher D Prone
(74) *Attorney, Agent, or Firm* — Quarles & Brady LLP

(57) ABSTRACT

Permanent magnets are implanted in bone to unload compressive forces at joints using the repulsive force therebetween. A porous metal container is implanted first and becomes fixed in place by bone growth. The permanent magnet is then inserted in the container and retained in place. A magnet prescription system includes a display and input device which enables a user to alter parameters such as magnet size, strength and placement and calculate and display the repulsive force that will result.

5 Claims, 10 Drawing Sheets

IMPLANTATION OF MAGNETS IN BONE TO REDUCE CONTACT PRESSURE

This application claims benefit of U.S. Provisional Application No. 60/326,122, filed on Sep. 28, 2001.

BACKGROUND OF THE INVENTION

The field of the invention is the implantation of permanent magnets in bone to reduce the contact pressure between bones at a joint or between a bone and a prosthetic device.

Primary osteoarthritis is a disabling condition, which destroys the joint surfaces through degenerative changes, as age advances. It is the leading cause of limitations in activities of daily living and is second only to heart disease in causing work disability. The direct traditional medical costs and indirect economic and wage loss from arthritis in individuals in the United States has reached an excess of $65 billion annually. In 1994, the Center for Disease Control, reported that by the year 2020, osteoarthritis will have the largest increase in the numbers of new patients of any disease in the United States.

Initial management of most arthritis patients includes changes in lifestyle, NSAIDs, analgesics, physical therapy, bracing and ambulatory aids. Surgical treatment comes into play only when consecutive treatment fails to improve the symptoms. Common surgical options include arthroscopic debridement of the knee, high tibial osteotomy, and unicompartmental or tricompartmental knee replacement, depending on the predominantly involved compartment. Surgical procedures, short of joint replacement surgery or high tibial osteotomy which include arthroscopic lavage, microfracture, chondrocyte or osteochondral transplants are not cost effective and have no reliable long term results.

High tibial osteotomy is mostly done in patients who have osteoarthritis and have varus malaligned knees. It relieves pressure from the medial joint line and redistributes the body weight passing through the knee so that the lateral compartment, which is relatively spared from the wear and tear process of osteoarthritis, can bear most of the weight. Pain is relieved and function is restored in more than 60% of the patients even 10 years after the operation. The results are best if at least 7 to 10 degrees of valgus alignment is achieved at operation and the weight of the person is not more than 30% of the ideal body weight. Clearly, procedures which reduce the pressure between arthritic bones reduces pain.

The idea of implanted magnets to produce forces between bones at a joint or between a bone and a prosthesis has been known for many years. The use of permanent magnets in bones to either assist in holding joints together or to reduce pressure between two bones at a joint or a bone and a prosthesis was disclosed initially in U.S. Pat. No. 4,024,588. More recently the use of arrays of permanent magnets implanted in bone have been disclosed in U.S. Pat. Nos. 5,507,835; 5,879,386; and 6,387,096 and published U.S. Appln. 2002/0032484A1. The permanent magnets are either mounted in prosthetic elements which are fastened to a bone, or the permanent magnets are encased in a biocompatible material and inserted into a hole drilled in the bone.

There are two practical problems with prior magnet implantation methods which have precluded their clinical use. First, there is no method suitable for clinical use to determine the strength of permanent magnets to be implanted and there is no suitable method for implanting the permanent magnets in bone.

SUMMARY OF THE INVENTION

The present invention is a method and apparatus for implanting permanent magnets in bone to produce a prescribed force therebetween. The invention is a magnet assembly comprised of: a porous container having a cavity therein for receiving a magnet and an opening at one end of the container; a permanent magnet disposed in the cavity; and a cover which fastens to the porous container for retaining the magnet in the cavity. A permanent magnet is implanted in bone by: drilling a hole in the bone for receiving the permanent magnet assembly at a prescribed location; inserting the container made of porous material into the hole; waiting for a period of time to allow bone to grow into the pores of the container to anchor it in place; and then inserting the permanent magnet in the container.

A general object of the invention is to implant permanent magnets in bone such that they remain in the desired location. Depending on the orthopedic objective, the prescribed force can exceed 100 pounds. This force is focused at magnets on the order of 1.0 cm in size. To prevent migration of the magnets, the container firmly attaches to the bone and provides a strong surface against which the confined magnet bears.

Another object of the invention is to enable implanted permanent magnets to be replaced. By housing the permanent magnet in a container with a removable cover, the implanted magnet can be easily replaced with another magnet of the same size but different strength. This may occur, for example, if a joint disease such as arthritis progresses and a magnet with a higher force is needed to reduce pain.

Another aspect of the invention is a magnet prescription system for designing the deployment of a pair of magnets across a joint which comprises: a monitor for displaying information; an input device for entering information into a computer; and a computer programmed to prompt a user to enter a set of variables associated with a repulsive force produced by two magnets, to calculate the repulsive force and display it on the monitor. The variables may also be displayed on the monitor and the user may change variables such as magnet spacing, magnet size and magnet strength and immediately see the resulting repulsive force.

An object of the invention is to enable a physician to properly prescribe magnets for implantation. Using medical images of the target joint, the physician first determines a repulsive force that will accomplish the clinical objective and the location of the magnets on each side of the joint. Magnet spacing, size and strength can then be varied using the magnet prescription system to obtain the desired repulsive force and joint loads.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
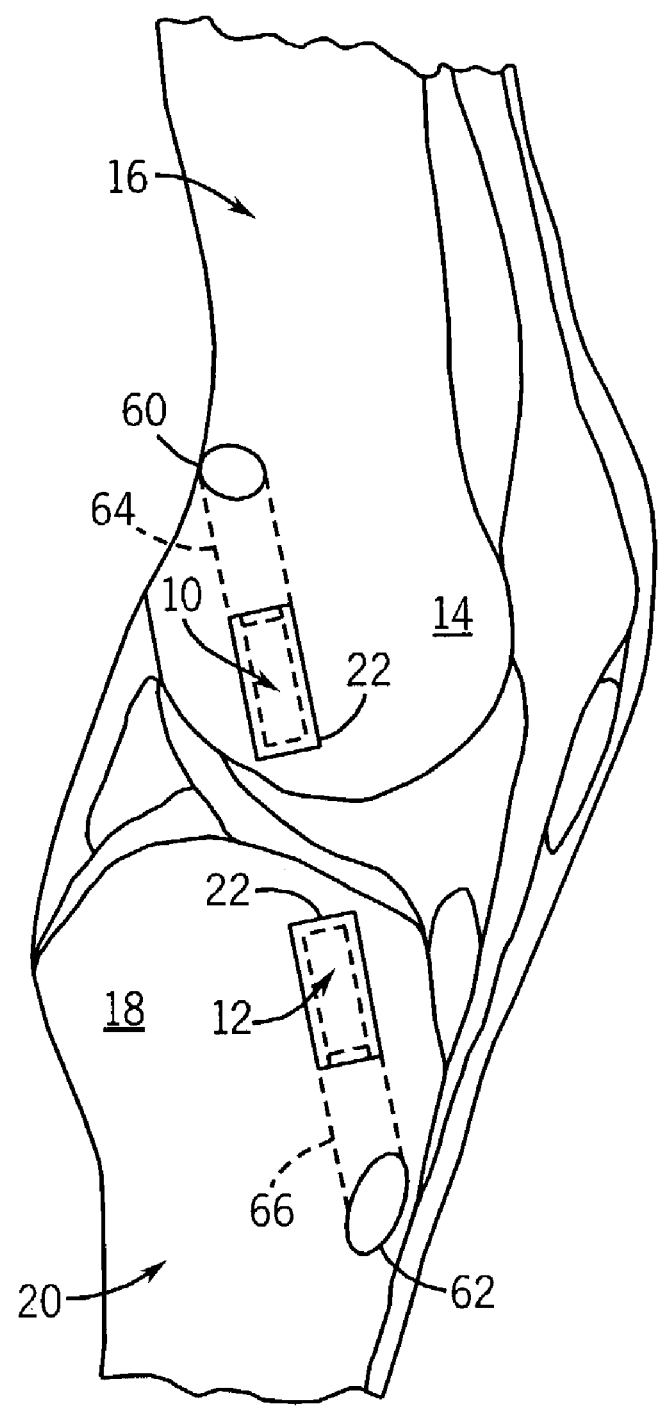
FIG. 1 is a sagittal view in cross-section of a knee joint showing the implantation of permanent magnets.

Referring particularly to FIG. 1, permanent magnets 10 and 12 are implanted in the medial epicondyle 14 of a femur 16 and the medial condyle 18 of a tibia 20. The magnets 10 and 12 are positioned such that their pole faces 22 of like polarity oppose each other across the knee joint. The magnets 10 and 12 are aligned such that they are directly across the joint from each other with their pole faces 22 substantially parallel to each other when the joint is in the maximum weight-bearing angle (i.e., approximately 20°). The resulting repulsive force $F_r$ between the magnets 10 and 12 serves to reduce the compressive force between the medial epicondyle 14 and media condyle 18. This in turn reduces the compressive forces in the knee to reduce pain caused by disease, trauma or joint degeneration. The required repulsive force $F_r$ is prescribed by the physician based on a diagnosis of the problem to be solved. The repulsive force $F_r$ produced is determined by a number of variables, including the strength of each magnet 10 and 12, the distance, or gap between their pole faces 22, and the size of the magnets 10 and 12.

Figure 2:
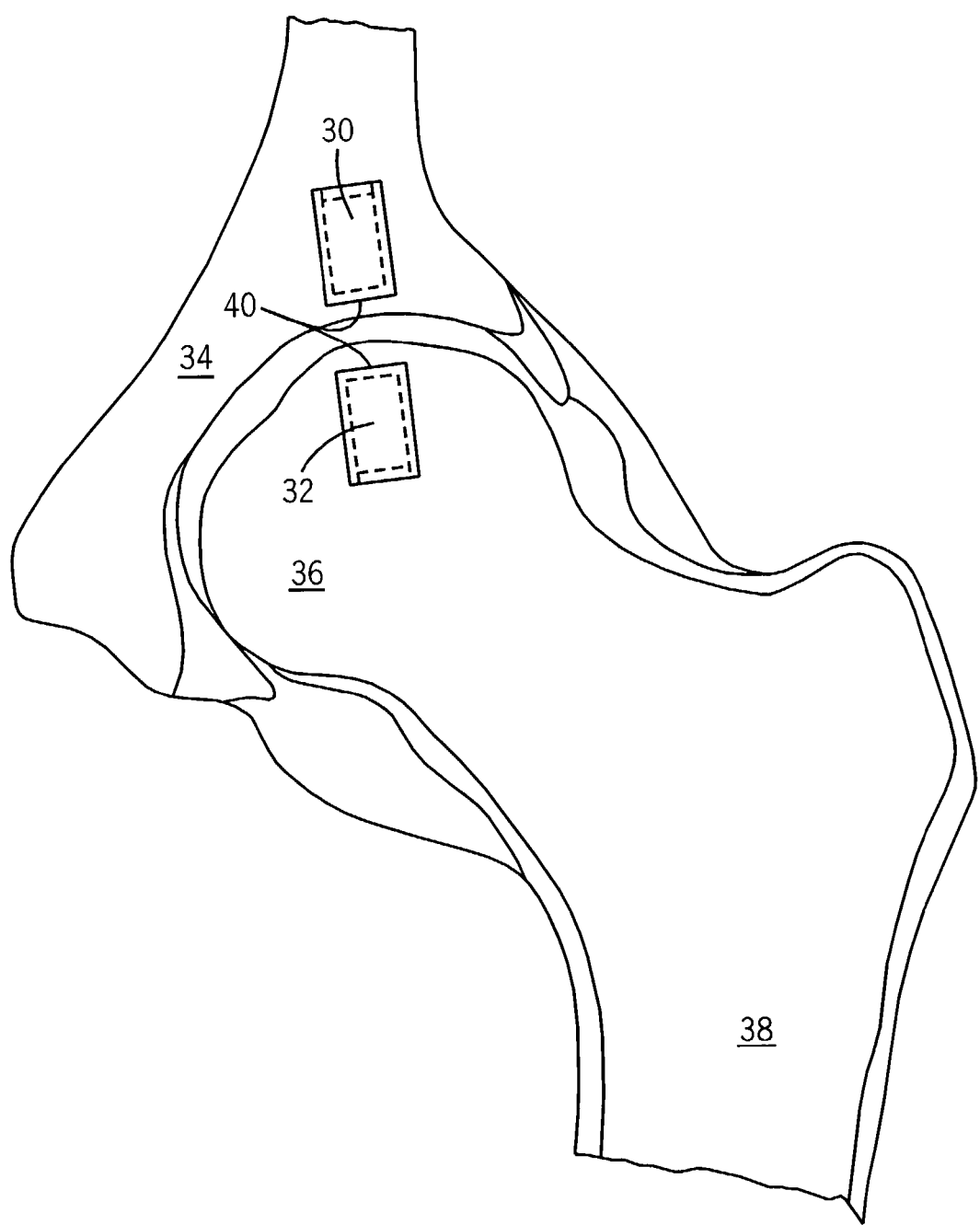
FIG. 2 is a sagittal view in cross-section of a hip joint showing the implantation of permanent magnets.

Referring particularly to FIG. 2, permanent magnets may be used in the hip joint to reduce contact pressure between the top of the femur head 36 and the upper acetabulum wall 34. In the implementation shown, magnets 30 and 32 are implanted in the acetabulum 34 and the head 36 of femur 38. The magnets 30 and 32 are positioned such that their opposing pole faces 40 of like polarity are aligned directly opposite each other and with pole faces 40 substantially parallel when the patient is in a standing position. The repulsive force $F_r$ produced by the magnets 30 and 32 is thus maximum when the patient is standing and it acts through a point on the top of the head 36 at which the compression forces on the hip joint are maximum. The repulsive force $F_r$ is prescribed by the physician to reduce this compressive force and thus reduce the pain that may be caused by disease, trauma or degeneration of the joint.

It should be apparent to those skilled in the art that pairs of permanent magnets may be implanted in other bones of the body to alleviate forces acting on other diseased, degenerated or traumatized joints. In addition to bone joints, pairs of magnets may be used to reduce pressure between a bone and a prosthesis. In such case, one magnet is implanted in the bone and the other magnet is built into the prosthesis.

Figure 3:
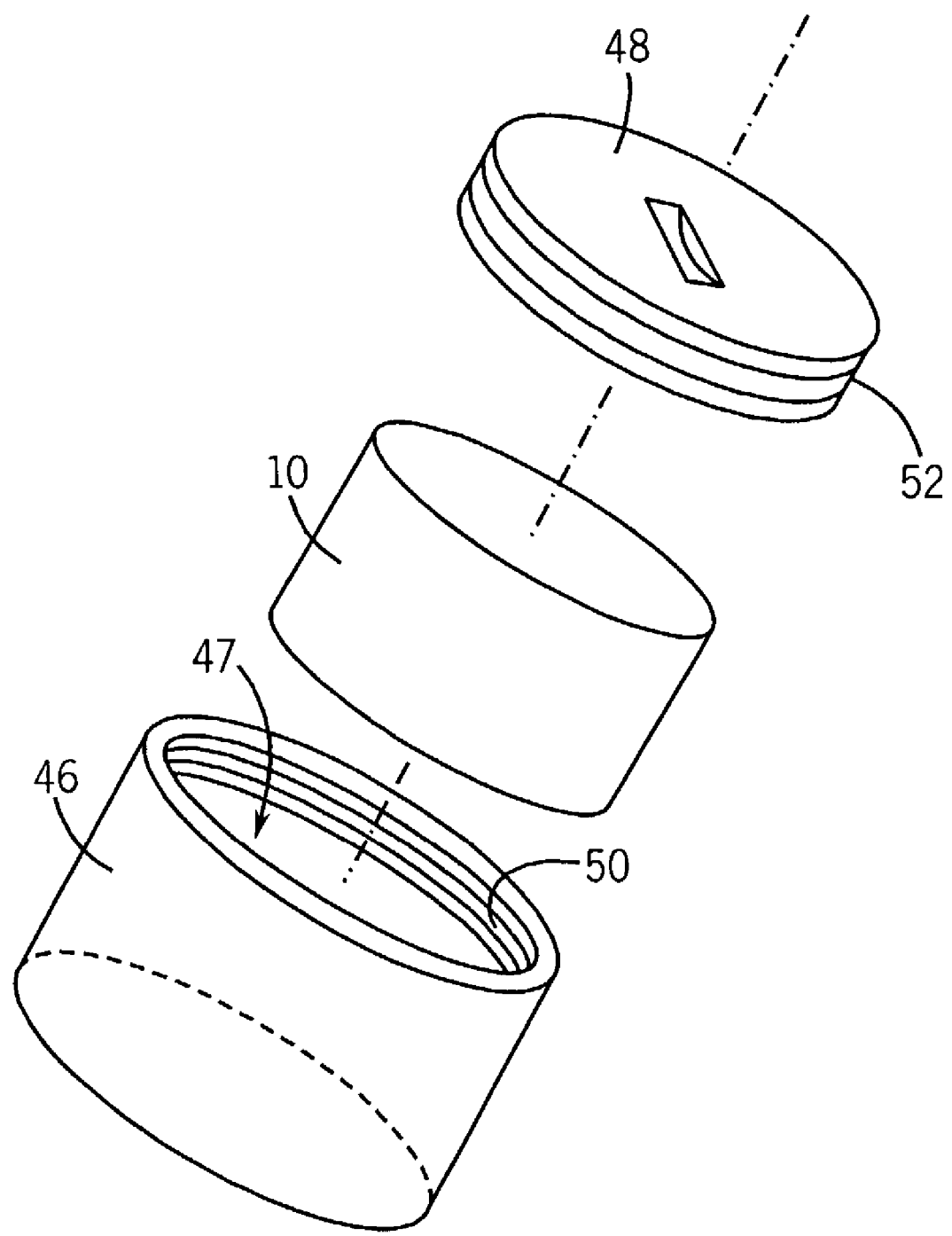
FIG. 3 is an exploded perspective view of a magnet assembly used in the implants of FIGS. 1 and 2.

The implanted magnets 10, 12, 30 and 32 form one element of a magnet assembly. One such magnet assembly is shown best in FIG. 3 for the circular, cylindrical shaped magnet 10. The magnet 10 is formed from a high energy magnetic material such as samarium-cobalt (SmCo5 or SmCo17) or neodymium-iron-boron (NdFeB), and its size may range from less than 1.0 cm to many cm in diameter and a length depending on the force to be produced. Materials having magnetization levels ranging from 223 to 382 KJ/m³ or 28 to 48 MGOe may be used to produce repulsive forces $F_r$ in the range applicable to orthopedics. The magnets are coated with a biocompatible polymeric material to inhibit corrosion by body fluids.

Each magnet assembly includes a container for the magnet comprised of a housing 46 and a cover 48. The housing 46 is circular cylindrical in shape and it defines a cavity 47 having a shape and size for receiving the magnet 10 and retaining it in place. The magnet 10 is received through a threaded opening 50 formed at one end of the housing 46. The cover 48 is screwed into the threaded opening 50, to retain the magnet 10 firmly in place inside the container. While the threaded attachment of the cover 48 is preferred, it should be apparent that other fastening mechanisms such as a snap action or a twist and lock mechanism are also possible.

The container housing 46 is formed from a porous metal material which is suitable for implantation. Such materials are well known in the art for coating devices implanted in bone. In addition to their biocompatibility, they are characterized by the growth of bone into the voids, or pores, formed in the material. After a period of 60 to 120 days, such bone growth firmly fixes the implant in place. Such porous metal materials are described, for example, in U.S. Pat. Nos. 4,693,721, and 5,958,314 and are commercially available from sources such as Zimmer, Inc. of Warsaw Ind. Since the cover 48 may be removed from the implanted housing 46 from time to time, it is made of a solid metal which does not bond to surrounding bone.

While a number of procedures can be used to implant the magnet assemblies in the prescribed locations, the preferred method is a minimally invasive approach which does not disturb the joint. Referring particularly to FIG. 1, the first surgical step of the procedure is to drill holes 60 and 62 in the respective bones 14 and 18 to form bone tunnels 64 and 66 that extend from their respective openings in the surfaces of the bones toward the bone surfaces at the joint. Each bone tunnel 64 and 66 stops short of the joint to form an end wall just beneath the bone surface. The magnet housings 46 are then inserted in the bone tunnels 64 and 66 with their threaded openings 50 accessible through the bone tunnels. The magnet housings 46 are thus implanted at the end of each bone tunnel 64 and 66, just beneath the surface of respective bones 14 and 18 at the knee joint. The joint may be x-rayed to determine the exact location of each magnet housing 46 and any necessary adjustments are made. This preliminary surgical step may then be completed, or a magnet 10 may be inserted into one of the magnet housings before completing the operation. No repulsive force is produced when only one magnet is inserted, and insertion of one magnet during the first operation simplifies the second operation described below.

The bone is allowed to grow into the pores of the housings 46 for a period of 60 to 120 days to secure them in place before any forces are applied. In a second medical procedure the tunnel openings 60 and 62 are re-exposed and prescribed magnets 10 and 12 are inserted into the housings 46. Of course, if one magnet 10 or 12 was inserted during the first operation, then only one magnet 10 or 12 need be inserted during the second operation. To reduce the repulsive force between the magnets during this procedure the joint is manipulated to a position in which the magnets are maximally spaced or misaligned. The covers 48 are screwed into place to retain the magnets in their housings 46 and further rotation of the covers 48 slides the magnets 10 and 12 against the enclosed ends of the housings 46 and against the increasing repulsive force. The second surgical procedure is then completed.

If at a later time the strength of the repulsive force $F_r$ needs adjustment, new magnets can be produced to replace those now in place. The tunnel openings 60 and 62 are exposed, the covers 48 unscrewed, and the old magnets removed. The new magnets are inserted as described above, and the surgical procedure terminated. The implanted magnet containers thus enable periodic changes to be easily made in the prescribed magnet strength in response to changes in the joint condition. For example, it may be necessary to increase the repulsive force $F_r$ over time in order to alleviate pain caused by a progressively worse disease.

A number of variations are possible from the preferred embodiment of the magnet assembly. In some applications it may be desirable to extend the axial dimension of the container by elongating the housing 46. This may be done, for example to shorten the distance between the opening in the housing 46 and the bone tunnel openings so that magnets may more easily be changed. In such case the magnet may be substantially shorter in length than the interior of the housing 46 and a means for retaining the magnet against the closed end of the housing 46 must be provided.

Figure 13:
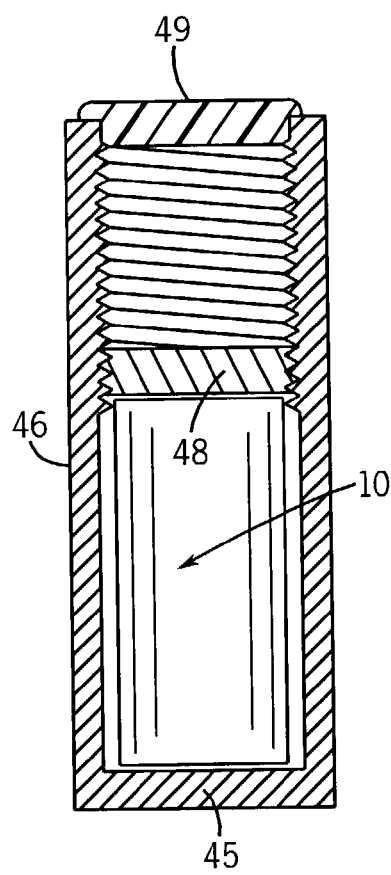
FIG. 13 is a cross-sectional view of a first alternative embodiment of the magnet assembly of FIG. 3.

One solution shown in FIG. 13 is to thread the interior of the housing 46 such that threaded cover 48 can be used to push the magnet 10 against the closed end 45. In this embodiment a cap 49 is friction fit into the open end of the housing 46 to prevent growth of bone into its interior.

Figure 14:
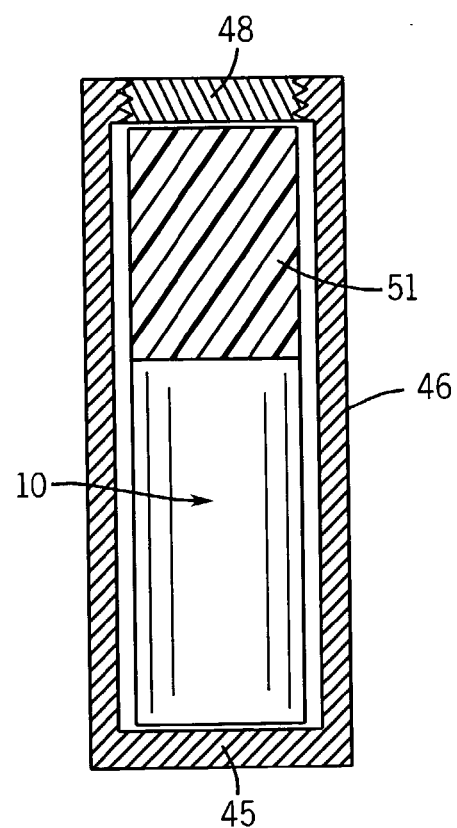
FIG. 14 is a cross-sectional view of a second alternative embodiment of the magnet assembly of FIG. 3.

Another solution shown in FIG. 14 is to employ a spacer 51 disposed between the cover 48 and the magnet 10. The length of the spacer is selected such that the magnet 10 is pushed firmly against the enclosed end 45 when the cover 48 is securely fastened to the housing 46.

Figure 4:
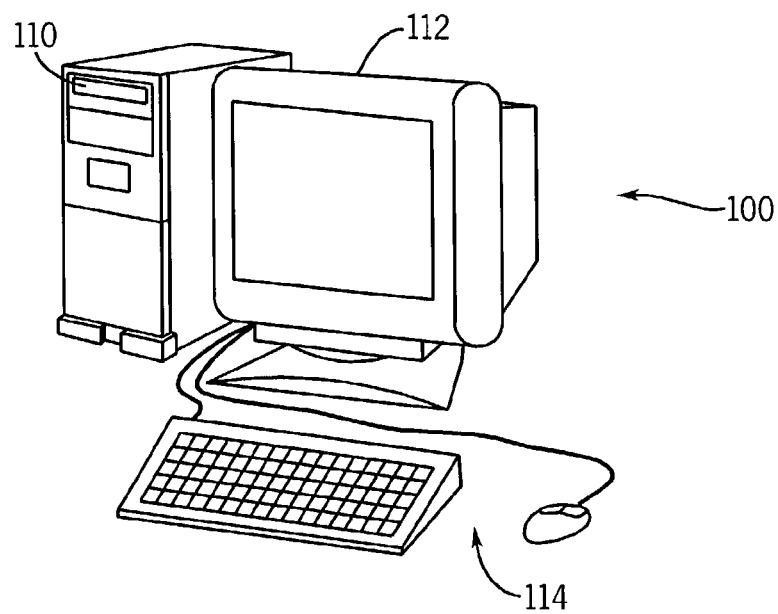
FIG. 4 is a pictorial view of a magnet prescription system used to determine the strength of implant magnets.

Referring particularly to FIG. 4, a magnet prescription system 100 is employed to determine the magnet strength and the other variables required to produce a prescribed repulsion force $F_r$. The prescription system 100 includes a mini-tower 110 which houses a processor and associated circuitry, memory, and peripheral interface circuits. One of the peripheral devices is a commercially available CRT monitor 112 which connects to a graphics circuit housed in the mini-tower 110, and another peripheral device is a keyboard and mouse 114 that connects to a PCI-based controller in the mini-tower 100. An operator may input data through the keyboard and control the position of a cursor on the monitor 112 using the mouse. A wide variety of processors may be employed in the mini-tower 110, and in the preferred embodiment a commercially available processor from Intel Corporation is used along with an operating system commercially available from Microsoft Corporation.

Figure 5:
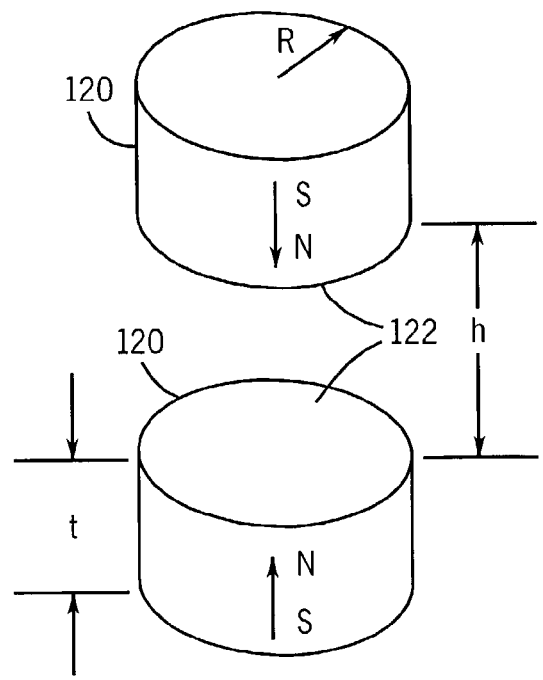
FIG. 5 is a pictorial representation of two cylindrical permanent magnets in which design variables are identified.

To understand the operation of the system 100 it is necessary to understand the physics involved with two implanted magnets. Referring particularly to FIG. 5, when two magnets 120 are oriented with like poles (N or S) near each other, their interacting magnet fields produce a repulsive force $F_r$ that acts between the magnets 120. With two cylindrical-shaped magnets 120 that are aligned as shown in FIG. 5 (i.e., their pole faces are aligned and parallel to each other), the repulsive force $F_r$ has a magnitude determined by the magnetization $M_s$ of the magnetic material, the radius of the magnets 120, the gap between pole faces 122 and the axial lengths of each magnet 120.

Figure 6:
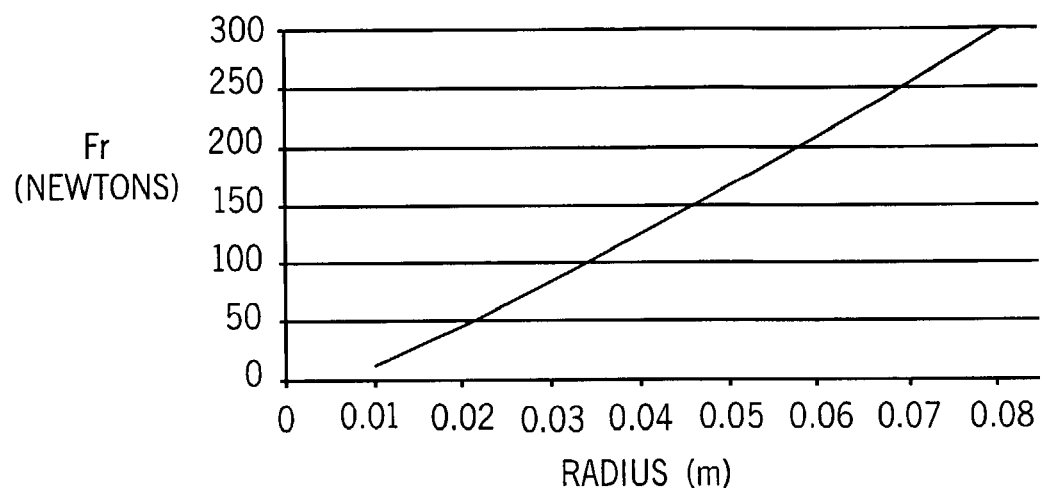
FIG. 6 is a graph illustrating how the repulsive force between the magnets in FIG. 5 change as a function of magnet radius.
Figure 7:
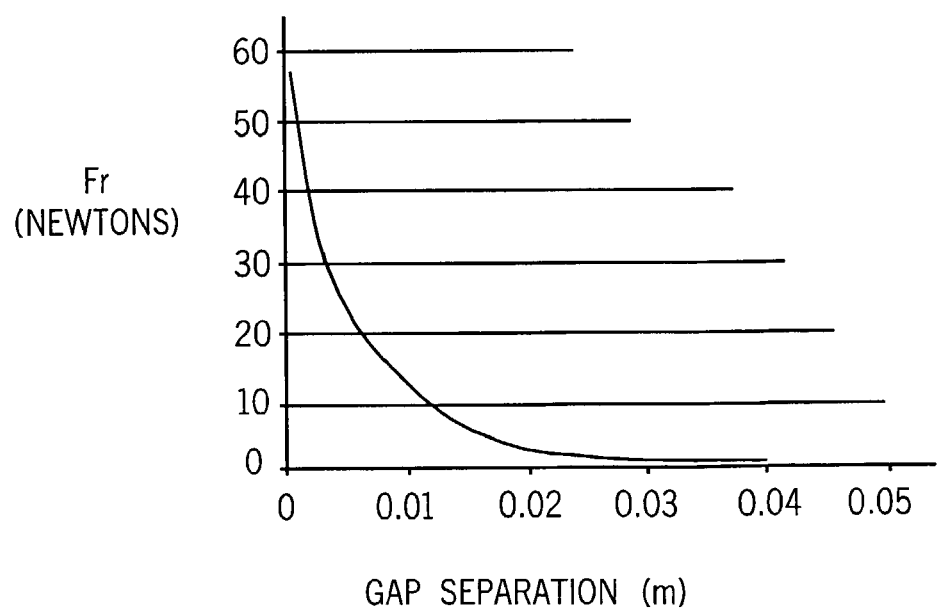
FIG. 7 is a graph illustrating how the repulsive force between the magnets in FIG. 5 change as a function of the gap between their pole faces.

A graph of the repulsive force $F_r$ as a function of magnet radius R is shown in FIG. 6 for 1 cm long magnets, spaced 1 cm apart and having a strength $M_s=750000$ A/m. A graph of the repulsive force $F_r$ as a function of gap size h is shown in FIG. 7 for a magnet having a radius and length of 1 cm and a strength $M_s=750000$ A/m.

Figure 8:
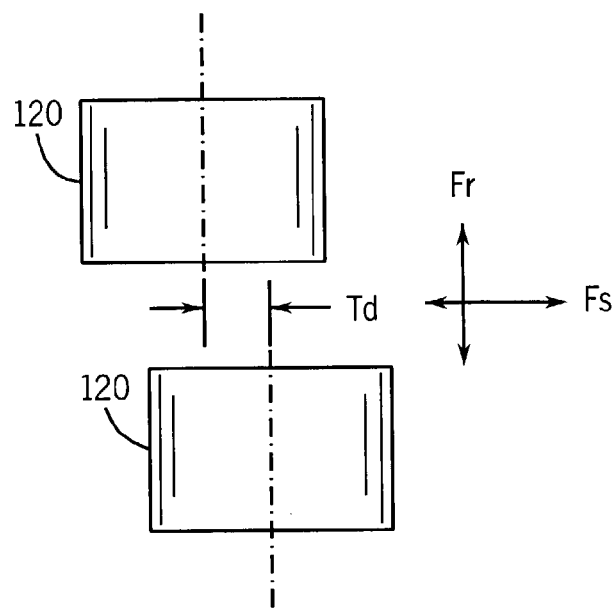
FIG. 8 is a pictorial view showing transverse displacement of the magnets of FIG. 5.
Figure 9:
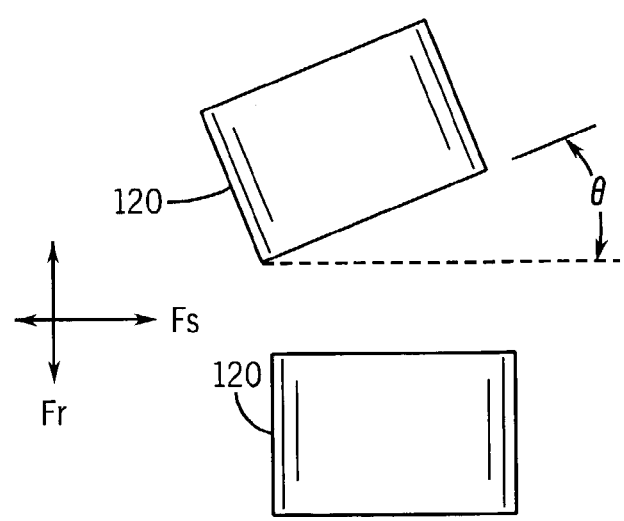
FIG. 9 is a pictorial view showing angular displacement of the magnets of FIG. 5.
Figure 10:
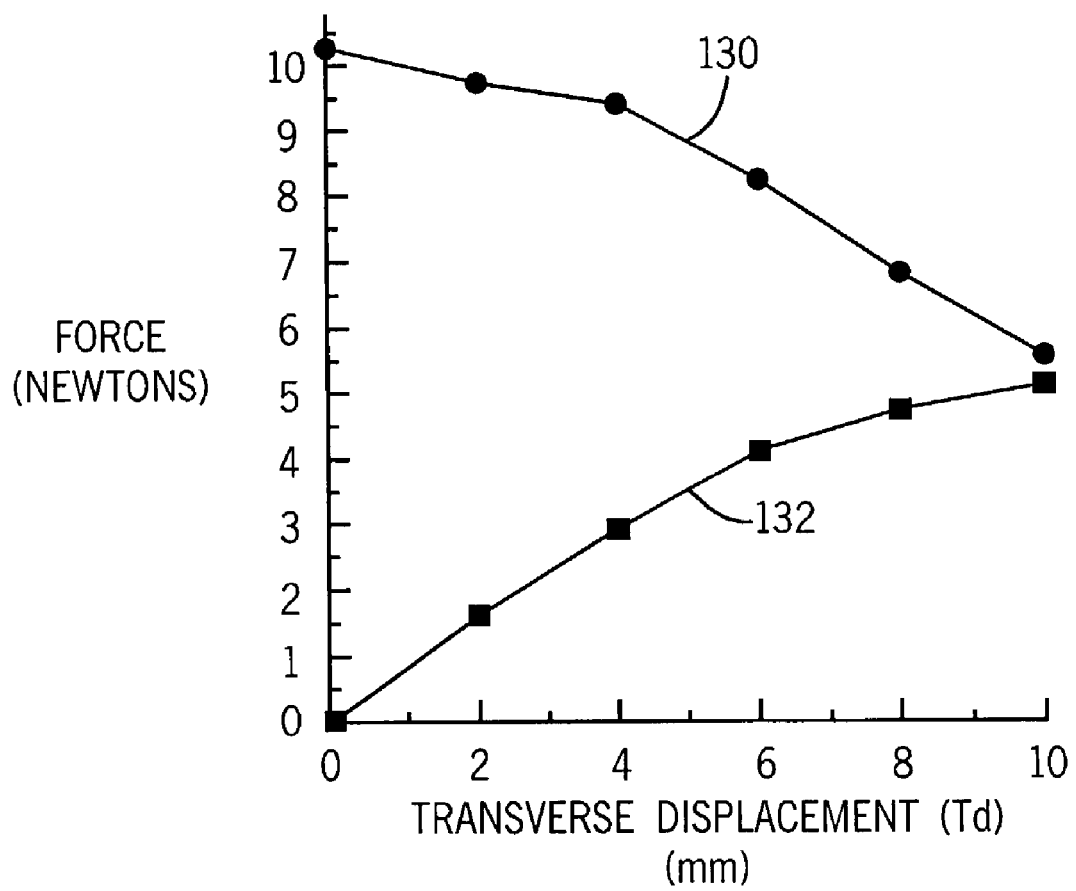
FIG. 10 is a graph illustrating the change in repulsive force between the magnets of FIG. 5 as a function of transverse or angular displacement.

When the magnets 120 become transversely misaligned as shown in FIG. 8, or angularly misaligned as shown in FIG. 9, the repulsive force $F_r$ reduced and a shear force $F_s$ is produced. Such misalignment may occur due to the normal motion at a joint as the associated bones move over their range of motion. The addition of the transverse displacement ($T_d$) shown in FIG. 8 and the angular misalignment (θ) shown in FIG. 9 reduces the repulsive force $F_r$ and increases the shear force $F_s$. FIG. 10 is a graphic representation of the changes in these forces as a function of transverse displacement ($T_d$), where graph 130 shows the drop in repulsive force $F_r$ as the displacement increases and graph 132 shows the increase in shear force $F_s$ as displacement increases. These graphs 130 and 132 depict forces for a very small pair of magnets having a radius (R), a length (t), and a gap (h) of 10 mm and a strength (Ms) of 750000 A/m.

It should be apparent that there are a large number of variables involved in the production of a prescribed repulse force $F_r$ between two implanted magnets. While one could limit the number of variables by fixing such parameters as magnet length or magnet radius or magnet strength, such limitations reduce the flexibility of precisely prescribing the magnets for the situation.

The magnet prescription system 100 is a tool which enables the physician or medical technician to determine the best combination of variables to be prescribed in a particular clinical application. As will be described in detail below, software in the system 100 enables the user to input values for the variables, and using these values, the system 100 calculates values for the forces $F_r$ and $F_s$ and displays them on the monitor screen 112.

Figure 11:
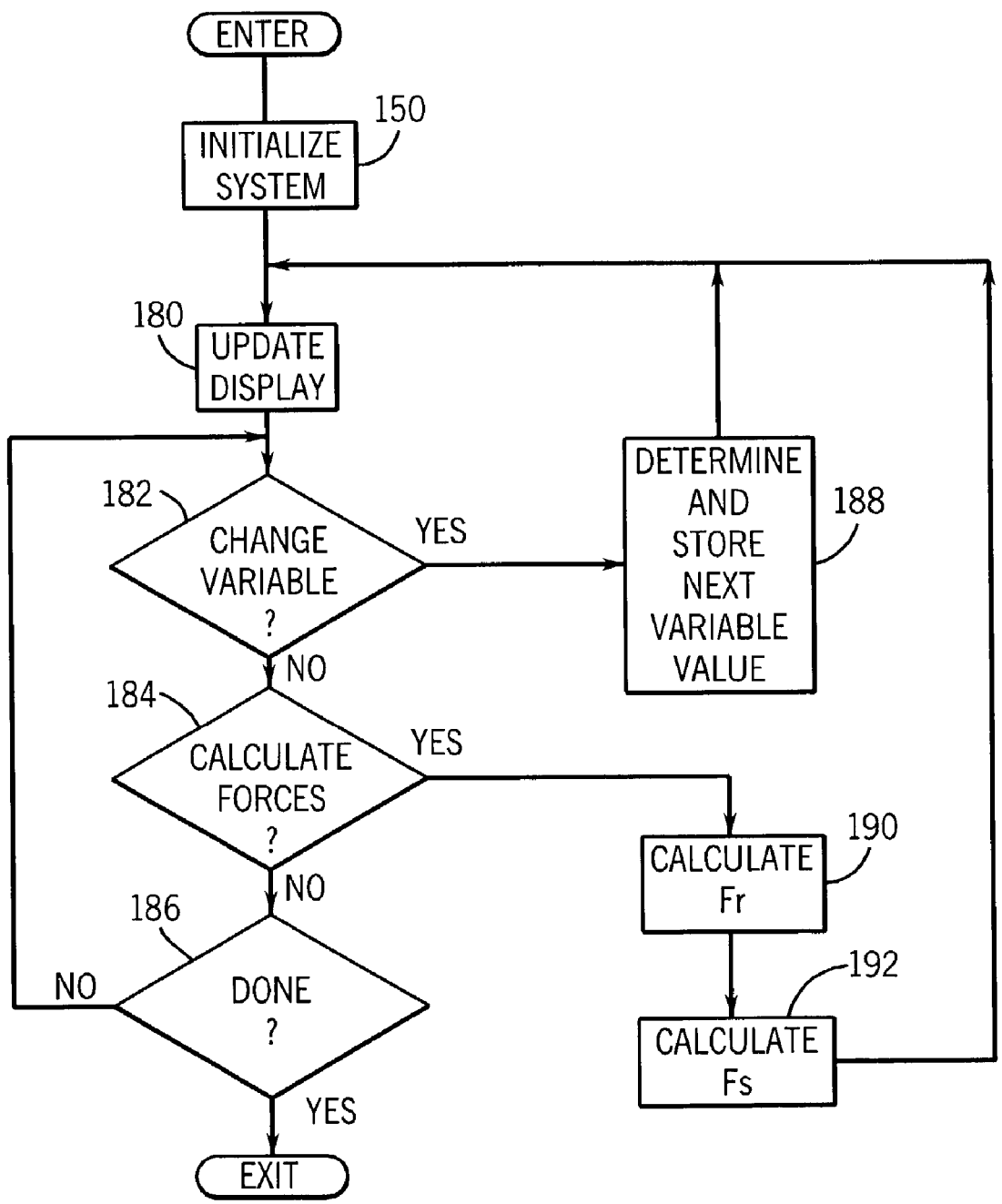
FIG. 11 is a flow chart of the functions performed in response to the execution of a program stored in the system of FIG. 4.
Figure 12:
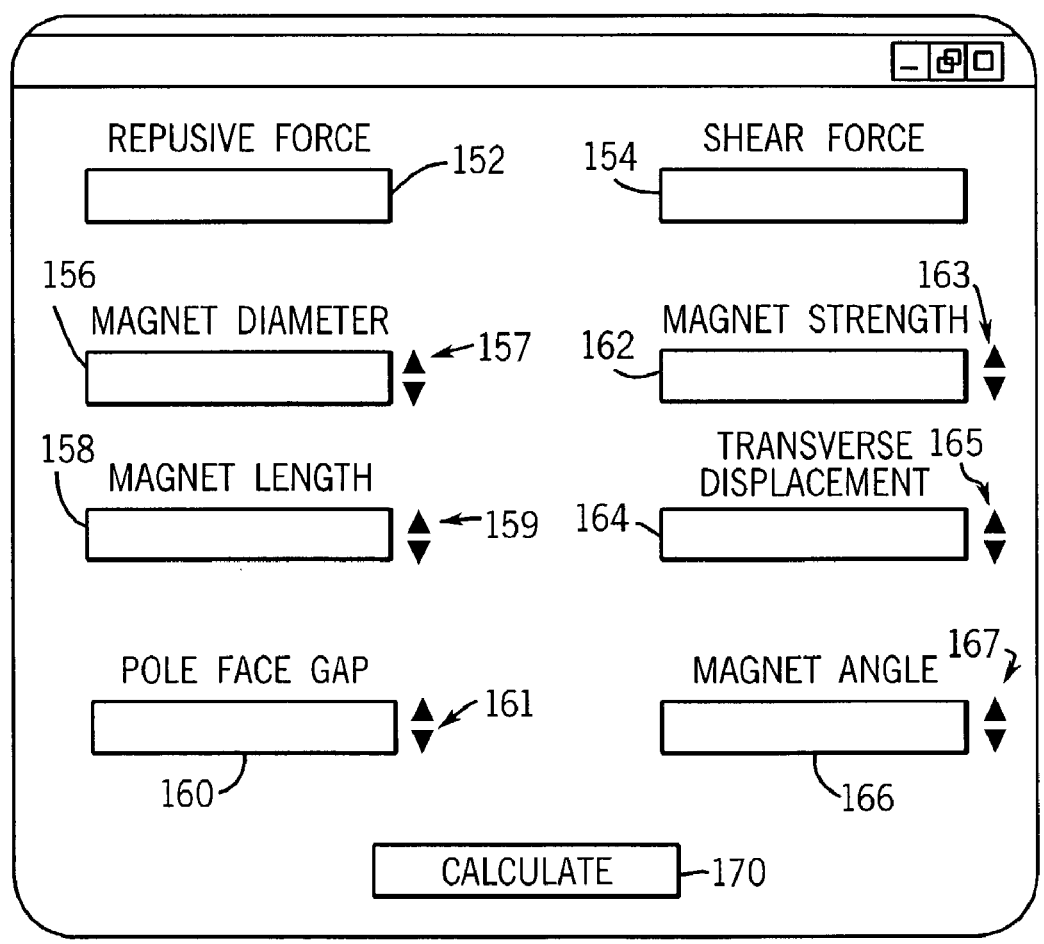
FIG. 12 is a pictorial representation of the information displayed on a system monitor when the program of FIG. 11 is executed.

Referring particularly to FIG. 11, when the system 100 is powered up it performs an initialization step indicated by process block 150 which establishes a number of data structures and produces an initial input display which is output to the monitor screen 112. This display is shown in FIG. 12 and includes two output regions 152 and 154 at which the calculated forces $F_r$ and $F_s$ are displayed. Six input regions 156, 158, 160, 162, 164 and 166 are displayed along with associated arrow buttons 157, 159, 161, 163, 165 and 167. By moving a cursor onto one of the arrow buttons with the mouse, the corresponding variable can be increased or decreased in value by clicking the appropriate up or down arrow. When the variables are set to the desired values, a "calculate" button 170 may be depressed and new force values are calculated and displayed at output regions 152 and 154. Variables can be changed at will and the calculate button 170 depressed to display the resulting forces $F_r$ and $F_s$. This process can be continued until the user is satisfied that the prescribed repulsive force $F_r$ can be produced with an appropriate set of variable values.

Referring back to FIG. 11, during initialization the initial variable values are set in the middle of their respective ranges and the display is updated as indicated by process block 180. A loop is then entered in which the system waits for a click on one of the variable arrow buttons as indicated at decision block 182, or a click on the calculate button 170 as indicated by decision block 184, or a click on the close window icon as indicated by decision block 186. If one of the variable arrow buttons is clicked as determined at decision block 182, the next value for the selected variable is determined at process block 188. In the case of some variables such as pole face gap, transverse displacement and magnet angle, the current variable value is simply incremented or decremented a preset amount depending on whether the up or down arrow is clicked. Other variables such as magnet size and strength have discrete values which are stored in tables. In this case the next variable value is the next entry in the table either above or below the current value as determined by which arrow button is clicked. The system then loops back to display the updated variable values at process block 180.

If the "calculate" button is clicked as determined at decision block 184, the value of the repulsive force $F_R$ is calculated as indicated at process block 190 using the current variable values. As indicated at process block 192, the value of the shear force $F_s$ is then calculated using the current variable values. The system then loops back to update the display at process block 180 with the new force values.

The system 100 assists a physician in planning the first surgical step described above, and it enables the magnet strength and length to be precisely determined before performing the second surgical step. Prior to the first surgery the location of magnets can be planned using medical images such as bi-planer radiographs, standing x-rays, CT or MRI of the subject joint. Various combinations of variables can be considered which will provide the prescribed repulsion force $F_r$ and enable choices as to precise magnet location. After the containers have been implanted, an image of the joint can be acquired and the precise location of the magnets determined prior to their actual insertion. The magnet strength and/or length may be adjusted to account for small misplacement of the containers during the first surgical step. In addition, images of the implanted containers can be acquired over the entire range of joint motion and both the repulsive force $F_r$ and the shear force $F_s$ calculated at different joint angles by taking transverse displacement ($T_d$) measurements and misalignment angle ($\theta$) measurements off the images. Any necessary adjustments can then be made to the permanent magnets before their actual implantation.

The invention claimed is:

1. A magnet assembly for implantation in bone adjacent a joint, the assembly comprising:
   a container capable of being implanted in bone adjacent a joint, the container formed of a porous material and having a cavity therein for receiving a permanent magnet through an opening at one end of the container and wherein the other end of the container is closed and directed toward the joint;
   a permanent magnet having a width of at least 1.0 centimeter disposed in the cavity at the closed end of the container; and
   a cover which is fastened to the container for retaining the permanent magnet in the cavity, wherein the cover fits in the opening and wherein the cover is not attached to the permanent magnet;
   wherein bone grows into the porous material of the implanted container to rigidly retain the container in a fixed location in the bone;
   wherein the permanent magnet creates a repulsive force in order to provide a treatment in which the bone is urged away from the joint to reduce contact pressure between the bone and the joint.

2. The magnet assembly as recited in claim 1 in which the porous material is a porous metal.

3. The magnet assembly as recited in claim 2 in which the metal is tantalum.

4. The magnet assembly as recited in claim 1 in which the opening is threaded and the perimeter of the cover is threaded such that the cover fastens to the container by engaging the threaded opening.

5. A magnet assembly for implantation in bone adjacent a joint, the assembly comprising:
   a container formed of a porous material capable of being implanted in bone adjacent a joint, the container formed of tantalum and having a cavity therein for receiving a permanent magnet through an opening at one end of the container and wherein the other end of the container is closed and directed toward the joint;
   a permanent magnet having a width of at least 1.0 centimeter disposed in the cavity at the closed end of the container; and
   a cover which is fastened to the container for retaining the permanent magnet in the cavity, wherein the cover fits in the opening and wherein the cover is not attached to the permanent magnet;
   wherein bone grows into the porous material of the implanted container to rigidly retain the container in a fixed location in the bone.

* * * * *

UNITED STATES PATENT AND TRADEMARK OFFICE
CERTIFICATE OF CORRECTION

PATENT NO. : 8,029,570 B2
APPLICATION NO. : 10/254232
DATED : October 4, 2011
INVENTOR(S) : Barnes et al.

It is certified that error appears in the above-identified patent and that said Letters Patent is hereby corrected as shown below:

Column 6, line 12 "$F_r$ reduced" should be --$F_r$ is reduced--

Signed and Sealed this
Twenty-fourth Day of April, 2012

David J. Kappos
*Director of the United States Patent and Trademark Office*